(12) United States Patent
Heylen et al.

(10) Patent No.: US 7,820,453 B2
(45) Date of Patent: Oct. 26, 2010

(54) CARDIOVASCULAR SAFETY ASSAY

(75) Inventors: Godelieve Irma Christine Maria Heylen, Westmalle (BE); Cornelus Gerardus Maria Janssen, Vosselaar (BE); Mirek Jurzak, Frankfurt am Main (DE); Henricus Petrus Martinus Maria Van Assouw, Oirschot (NL)

(73) Assignee: Janssen Pharmaceutica N.V., Beerse (BE)

( * ) Notice: Subject to any disclaimer, the term of this patent is extended or adjusted under 35 U.S.C. 154(b) by 293 days.

(21) Appl. No.: 11/593,399

(22) Filed: Nov. 6, 2006

(65) Prior Publication Data

US 2008/0193924 A1 Aug. 14, 2008

Related U.S. Application Data

(62) Division of application No. 10/483,617, filed as application No. PCT/EP2002/07364 on Jul. 2, 2002, now abandoned.

(30) Foreign Application Priority Data

Jul. 13, 2001 (EP) ................................. 01202689

(51) Int. Cl.
 G01N 33/567 (2006.01)
 G01N 33/53 (2006.01)
 C12Q 1/02 (2006.01)
 G01N 33/566 (2006.01)

(52) U.S. Cl. .......................... 436/504; 435/7.1; 435/7.8; 435/29; 436/501

(58) Field of Classification Search ........................ None
See application file for complete search history.

(56) References Cited

U.S. PATENT DOCUMENTS 4,568,649 A 2/1986 Bertoglio-Matte

FOREIGN PATENT DOCUMENTS

WO 0070079 11/2000
WO WO 02/42735 5/2002

OTHER PUBLICATIONS

Wells. Additivity of Mutational Effects in Proteins; Biochemistry, vol. 29, No. 37 (1990) pp. 8509-8517.*
Seffernick et al. Melamine Deaminase and Atrazine Chlorohydrolase: 98 Percent Identical but Functionally Different; Journal of Bacteriology, vol. 183, No. 8 (2001) pp. 2405-2410.*
Chiu et al. Validation of A [H3]Astemizolebinding Assay in HEK293 Cells Expressing Herg K+ Channels; Journal of Pharmacological Sciences, vol. 95 (2004) pp. 311-319.*
Zhou et al. Block of Herg Potassium Channels by the Antihistamine Astemizole and Its Metabolites Desmethylastemizole and Norastemizole; Journal of Cardiovascular Electrophysiology, vol. 10, No. 6 (1999) pp. 836-843.*

Taglialatela, M. et al. "Cardiac Ion Channels and Antihistamines: Possible Mechanisms of Cardiotoxicity". Clinical and Experimental Allergy, vol. 29, No. Suppl. 3, Jul. 1999, pp. 182-189. XP002198163.
Yap, Y.G. et al. "Arrhythmogenic Mechanisms of Non-Sedating Antihistamines". Clinical and Experimental Allergy. vol. 29, No. Suppl. 3, Jul. 1999, pp. 174-181. XP002198165.
Drici, M.D. et al. "Cardiac K+ channels and Drug-Acquired Long QT Syndrome". Therapie. New England 2000 vol. 55, No. 1. XP002198169.
Altschul, Stephen F. et al. "Gapped Blast and PSI-Blast: A New Generation of Protein Database Search Programs". Nucleic Acids Research, 1997, vol. 25, No. 17, pp. 3389-3402, Oxford University Press, University Park, PA., USA.
Dall'Asta, Valeria et al. "Membrane Potential Changes Visualized in Complete Growth Media through Confocal Laser Scanning Microscopy of bis-Oxonol-Loaded Cells". Experimental Cell Research, 231, 1997, pp. 260-268, Parma, Italy.
Chadwick, Christopher C. et al. "Identification of a Specific Radioligand for the Cardiac Rapidly Activating Delayed Rectifer K+ Channel". Circulation Research, Mar. 1993, vol. 72, No. 3, pp. 707-714, Alnwick Reseach Center (UK).
Claycomb, William C. et al. "HL-1 Cells: A Cardiac Muscle Cell Line that Contracts and Retains Phenotypic Characteristics of the Adult Cardiomyocyte". Proceedings of the National Academy of Sciences of the United States, vol. 95, No. 6, Mar. 17, 1998, pp. 2979-2984. XP002198161.
Netzer, Rainer et al. "Screening Lead Compounds for QT Interval Prolongation". Drug Discovery Today, vol. 6, No. 2, 2001, pp. 78-84. XP002198162.
Finlayson, Keith et al. "3HDofetilide Binding to HERG Transfected Membranes: A Potential High Throughput Prelinical Screen". European Journal of Pharmacology, vol. 430, No. 1, 2001, pp. 147-148. XP002198164.
Bischoff, Ulrike et al. "Effects of Fluoroquinolones on HERG Currents". European Journal of Pharmacology. vol. 406, No. 3, 2000, pp. 341-343. XP002198166.
Jones, Stephen E. et al. Inhibition of the Rapid Component of the Delayed-Rectifier K+ Current by Therapeutic Concentrations of the Antispasmodic Agent Terodiline. vol. 125, No. 6, Nov. 1998, pp. 1138-1143, XP002198167.
Rampe, David et al. "The Antipsychotic Agent Sertindole is a High Affinity Antagonist of the Human Cardiac Potassium Channel HERG". Journal of Pharmacology and Experimental Therapeutics, vol. 286, No. 2, Aug. 1998, pp. 788-793. XP002198168.
In the U.S. Patent and Trademark Office, Non-Final Office Action in re: U.S. Appl. No. 10/483,617 dated Jan. 12, 2006, 15 pages.
In the U.S. Patent and Trademark Office, Final Office Action in re: U.S. Appl. No. 10/483,617 dated May 5, 2006, 11 pages.
In the U.S. Patent and Trademark Office, Advisory Action in re: U.S. Appl. No. 10/483,617 dated Sep. 7, 2006, 3 pages.

(Continued)

Primary Examiner—Rebecca E. Prouty
Assistant Examiner—Paul C. Martin
(74) Attorney, Agent, or Firm—Patton Boggs LLP

(57) ABSTRACT

The present invention provides assays and kits for the screening of test compounds for their capability to induce cardiotoxicity in a subject. Said assays and kits are based on the finding that the interaction of astemizole with the HERG potassium channel can be exploited to predict cardiotoxicity of compounds during the development of new therapeutics and other agents.

5 Claims, 2 Drawing Sheets

OTHER PUBLICATIONS

Bakibaev et al., Methods for the Synthesis of Nitrogen-Containing Heterocycles using Ureas and Related Compounds, Russian Chemical Reviews (1998), 67(4):333-352, abstract only.

Dascal N., The Use of Xenopus Oocytes for The Study of Ion Channels, Crit.Rev.Biochem. (1987), 22(4):317-387.

Gerlt et al., Can Sequence Determine Function?, Genome Biology (2000), 1(5).

Haverkamp et al., The Potential for QT Prolongation and Pro-Arrhythmia by Non-Anti-Arrhythmic Drugs: Clinical and Regulatory Implications Report on a Policy Conference of the European Society of Cardiology, Cardiovascular Research (2000), 47:219-233.

Thijssen et al., Synthesis of 3H and 14C-Labeled Astemizole (R43512); Journal of Labeled Compounds and Radiopharmaceuticals (1983), 20(7):861-868.

Tsien et al., FRET for Studying Intracellular Signalling, Trends Cell Biology (1993), 3:242-245.

Zhou et al., Properties of HERG Channels Stably Expresses in HEK 293 Cells Studied at Physiological Temperature, Biophysical Journal (1998), 74:230-241.

International Search Report dated Dec. 2, 2002 for related International Application No. PCT/EP02/07364.

* cited by examiner

CARDIOVASCULAR SAFETY ASSAY

CROSS REFERENCE TO RELATED APPLICATIONS

This application is a Divisional of U.S. application Ser. No. 10/483,617, filed Jan. 13, 2004, and now abandoned, which is a 371 National Stage Entry of PCT/EP02/07364, filed Jul. 2, 2002, which claims priority to European Patent Application no. 01202689, filed Jul. 13, 2001, the entire contents of which are incorporated by reference herein.

The present invention relates to the field of cardiovascular safety assays and provides assays and kits for the screening of test compounds for their capability to induce cardiotoxicity in a subject. Said assays and kits are based on the finding that the interaction of astemizole with the HERG potassium channel can be exploited to predict potential cardiotoxicity of compounds during the development of new therapeutics and other agents. The present invention finds particularly advantageous use in high throughput screening of chemical compound libraries.

BACKGROUND OF THE INVENTION

Evidence has accrued that several drugs may prolong cardiac repolarisation (hence, "measured as" the QT interval of the surface electrocardiogram) to such a degree that potentially life-threatening ventricular arrhythmias e.g. torsades de pointes (TdP) may occur, especially in case of overdosage or pharmacokinetic interaction.

The number of drugs reported to induce QT interval prolongation with or without TdP continues to increase (W. Haverkamp et al. (2000) Cardiovascular Research 47, 219-233). As many as 50 clinically available or still investigational non-cardiovascular drugs and cardiovascular non-anti-arrhythmic drugs have been implicated. A number of drugs, both old and new, have either been withdrawn from the market or have had their sale restricted. Of concern is the interval, usually measured in years, from the marketing of these drugs to initial recognition of their association with QT interval prolongation and/or TdP. It would therefore be beneficial to investigate any new chemical entity for this potential side effect before its first use in man at an early stage of the development of new therapeutics and/or other agents.

A key component in the present development of new therapeutic agents consists of High Throughput Screening (HTS) of chemical compound libraries. Pharmaceutical companies have established large collections of structurally distinct compounds, which act as the starting point for drug target lead identification programs. A typical corporate compound collection now comprises between 100,000 and 1,000,000 discrete chemical entities. While a few years ago a throughput of a few thousand compounds a day and per assay was considered to be sufficient, pharmaceutical companies nowadays aim at ultra high throughput screening techniques with several hundreds of thousands of compounds tested per week. In a typical HTS related screen format, assays are performed in multi-well microplates, such as 96, 384 or 1536 well plates. The use of these plates facilitates automation such as the use of automated reagent dispensers and robotic pipetting instrumentation. Further, to reduce the cycle time, the costs and the resources for biochemicals such as recombinant proteins, HTS related screens are preferably performed at room temperature with a single measurement for each of the compounds tested in the assay.

A decisive criterion in the lead evaluation process will be an early recognition of their potential association with QT prolongation and/or TdP. However, there are currently no reliable, fast, easy screening methods available to assess cardiotoxicity, which can cope with the number of compounds identified in the currently deployed HTS techniques. It is an object of this invention to solve this problem in the art by providing assays and kits which are based on the finding that the interaction of astemizole with the HERG potassium channel can be exploited to predict cardiotoxicity of compounds during the development of new therapeutics and other agents.

The currently available in vitro models comprise heterologous expression systems, disaggregated cells, isolated tissues and the isolated intact (Langendorf-perfused) heart. In all models the effect of potassium current blockade is assessed by measurement of either ionic currents using two-electrode voltage clamp recordings (Dascal N. (1987) Crit. Rev. Biochem 22, 341-356) or patch-clamp recordings (Zhou Z. et al., (1998) Biophysical Journal 74, 230-241), of membrane potentials using microelectrodes or confocal microscopy (Dall'Asta V. et al. (1997) Exp. Cell Research 231, 260-268). None of the aforementioned methods can be used in an HTS screen in view of the complexity of the experimental procedures, the slow cycling times, the nature of the source materials (i.e. isolated tissues and disaggregated cells thereof) and the reliability of the test results.

The present inventors surprisingly found that a binding assay using labeled astemizole as a specific ligand for the HERG channel can be used to predict the potential association of compounds with QT prolongation and/or TdP. This binding assay solves the aforementioned problems and can be deployed in an HTS related screen format.

A similar assay has been described by Chadwick C. et al. (Chadwick C. et al., (1993) Circulation Research 72, 707-714) wherein [$^3$H]-dofetilide has been identified as a specific radioligand for the cardiac delayed rectifier K$^+$-channel. This article further demonstrates a good correlation between dofetilide displacement and potassium channel blocking activity of a number of antiarrhytmic compounds. This binding assay facilitates the characterization of drug-channel interactions at the molecular level.

In this assay labeled dofetilide has been prepared from the dibromo precursor by $^3$H-exchange yielding the incorporation of two $^3$H-labels per molecule. There is a direct correlation between the number of $^3$H-labels per molecule and the sensitivity of the binding assay. The present invention provides an improved binding assay over the above, as the use of a desmethylastemizole precursor in a reaction with [3$^3$H]-methyliodide resulted in the incorporation of three $^3$H-labels per molecule astemizole. The specific activity of the thus obtained radioligand is 1.5-2 times higher than the specific activity of [$^3$H]-dofetilide.

Further, the dofetilide assay could not be used in an HTS related screen format since the ventricular myocytes isolated from adult male guinea pigs had to be used within 6 hours of isolation. In addition only 36% of the isolated cells were viable and could be used in the binding assay. In order to be used in an HTS related screen, the starting material should be readily available and in sufficient amounts. The present invention solves this problem as membrane preparations of HEK293 cells, stably expressing the HERG potassium channel, are used. Said cells can be maintained in culture in sufficient amount avoiding the need and supply of animal models and as cell membranes are used in the binding assay, the latter can be stored in binding assay ready aliquots at −80° C. for later use. A further drawback of the dofetilide binding assay described by Chadwick et al. has to do with the incubation protocol. As viable myocytes are used, the incubation has to be performed at the physiological temperature of 34° C. The latter undoubtedly increases the costs, possible cycle time and complexity of the assay if to be performed in an HTS related screen format. The present invention solves this problem as it was surprisingly demonstrated that the membrane preparations could be incubated at room temperature. Espescially in light of a study by Zhoe Z. et al. Zhou Z. et al., (1998) Biophysical Journal 74, 230-241) which concluded that the kinetic properties measured for HERG are markedly dependent on temperature and that differences observed in several reports, are diminished when studies are performed at physiological temperatures, i.e. 35° C.

This and other aspects of the invention will be described herein below.

SUMMARY OF THE INVENTION

The present invention provides an assay for screening test compounds for their capability to induce cardiotoxicity in a subject, the method comprising incubating a source containing HERG or a fragment thereof with a reference compound and the test compound, for a time sufficient to allow binding of the reference compound and of the test compound with the HERG polypeptide channel and measuring the effect of the test compound on the amount of reference compound bound to HERG.

In a preferred embodiment of this invention, the assay consists of incubating membrane preparations of cells, preferably HEK293 cells, expressing on the surface thereof the HERG polypeptide channel comprising the amino acid sequence of SEQ ID NO:2 or a fragment thereof; with a labeled reference compound. Wherein said labeled reference compound is a drug capable to induce cardiac arrhythmia in a subject, preferably said labeled reference compound is [$^3$H]-astemizole. Incubating the above together with the test compound and measure the effect of the test compound on the amount of reference compound bound to the HERG polypeptide channel. In a further embodiment the means of measurement consist of separating means to remove the excess of unbound labeled reference compound from the incubation mixture and of means for detection of the labeled reference compound wherein the latter preferably consists of radiolabeled measurement using scintillation counting.

The invention further provides a high-throughput assay for screening compounds for their capability to induce cardiotoxicity in a subject, the assay comprising;

a) contacting membrane preparations of cells expressing on the surface thereof HERG polypeptide channels having an amino acid sequence that is at least 80% identical to that of SEQ ID NO:2 or fragments thereof, with a labeled reference compound for a time sufficient to allow binding of the reference compound with the HERG polypeptide channel;

b) contacting membrane preparations of cells expressing on the surface thereof HERG polypeptide channels having an amino acid sequence that is at least 80% identical to that of SEQ ID NO:2 or fragments thereof, with the labeled reference compound of step a) together with the test compound for a time sufficient to allow binding of the reference compound and of the test compound with the HERG polypeptide channel;

c) measuring the amount of labeled reference compound bound to the HERG channel in step a);

d) measuring the amount of labeled reference compound bound to the HERG channel in step b); and e) compare the amount of labeled reference compound bound to the HERG channel measured in step a) with the amount of labeled reference compound bound to the HERG polypeptide channel measured in step b).

In a preferred embodiment of the high-throughput screening assay, the membrane preparations are derived from cells, preferably HEK293 cells, expressing on the surface thereof HERG polypeptide channels encoded by the amino acid sequence consisting of SEQ ID NO:2. In a further embodiment of the high-throughput screening assay the labeled reference compound is astemizole, preferably [$^3$H]-astemizole.

The present invention also encompasses kits for screening compounds for their capability to induce cardiotoxicity in a subject as well as the use of reagents, including polynucleotides, polypeptides and suitable reference compounds in the assays of the present invention.

DETAILED DESCRIPTION

Figure 1:
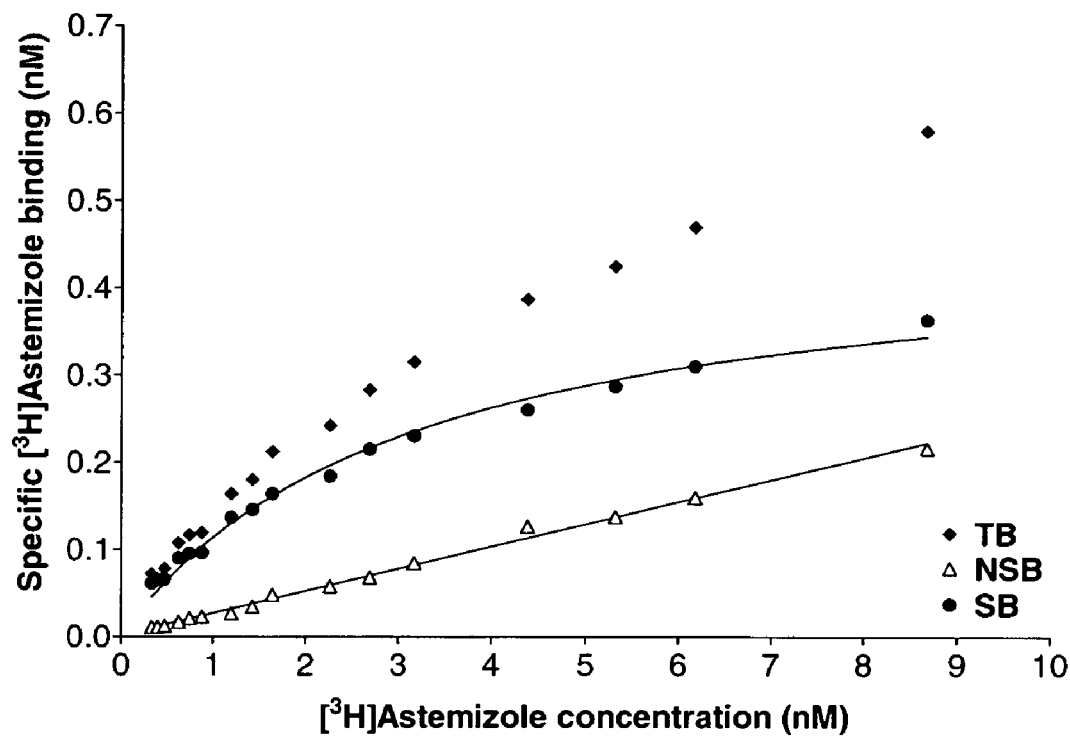
FIG. 1A shows the saturation binding of [$^3$H]-astemizole to cell membrane preparations of HEK293 cells stably transfected with the HERG channel cDNA. TB represents Total Binding measured, NSB represents Non Specific Binding measured and SB represents Specific Binding measured.
FIG. 1B shows the Scatchard plot for the saturation binding experiments. From the fitted line a $K_D$ of 3.07±2.26 nM (n=11) could be determined with a $B_{max}$ (Maximal Binding) of 3260±900 fmol/mg protein (n=11).
Figure 1:
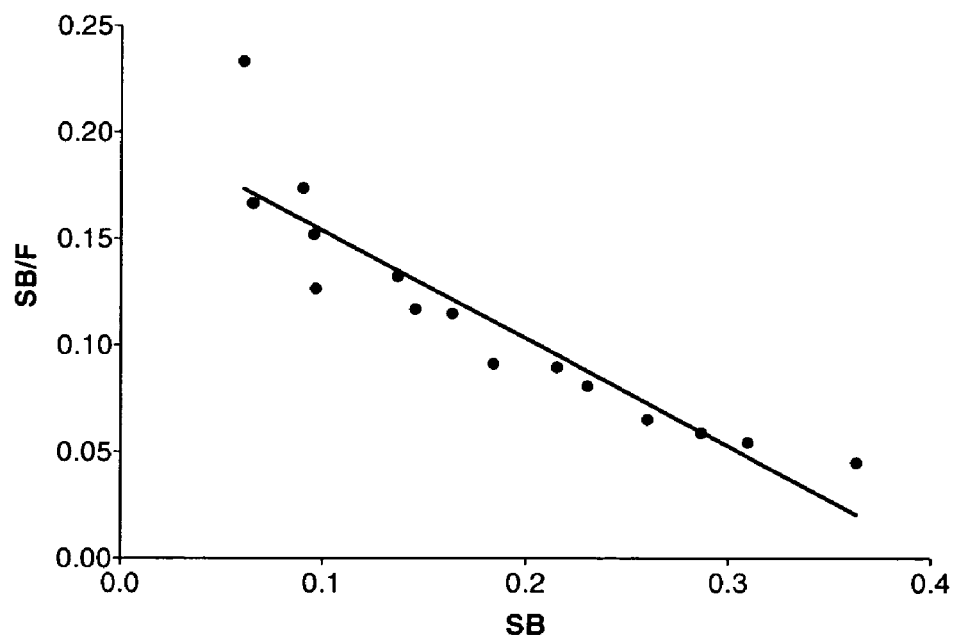

The present invention relates to the field of cardiovascular safety assays and provides assays and kits for the screening of test compounds for their capability to induce cardiotoxicity in a subject. Said assays and kits are based on the finding that the interaction of astemizole with the HERG potassium channel can be exploited to predict cardiotoxicity of compounds during the development of new therapeutics and other agents. The present invention finds particularly advantageous use in high throughput screening of chemical compound libraries.

In one embodiment of the present invention, the assay for screening test compounds comprises: a) incubating a source containing HERG or a fragment thereof with i) a reference compound, ii) the test compound; and b) measuring the effect of the test compound on the amount of reference compound bound to HERG.

In a specific embodiment of the present invention the assays are used to assess the capability of the test compounds to induce cardiac arrhythmia in a subject.

As used herein the term "test compound" refers to a chemically defined molecule whose cardiac arrhythmia inducing capability is assessed in an assay according to the invention. Test compounds include, but are not limited to, drugs, ligands (natural or synthetic), polypeptides, peptides, peptide mimics, polysaccharides, saccharides, glycoproteins, nucleic acids, polynucleotides and small organic molecules. In one embodiment test compounds comprise an existing library of compounds. In another embodiment, test compounds comprise a novel library of compounds.

As used herein the term "reference compound" refers to a drug capable to induce cardiotoxicity in a subject. Reference compounds include, but are not limited to, astemizole, terfenadine, erythromycin, sparfloxain, probucol, terodiline and sertindole.

As used herein the term "HERG" refers to the Human Ether-a-go-go-Related Gene channel. It is a delayed rectifier potassium channel that plays a role in the control of action potential repolarization in many cell types. HERG was originally cloned from human hippocampus and it is strongly expressed in the heart. The HERG polypeptides according to the invention include isolated and purified proteins having an amino acid sequence that is at least 80% identical to that of SEQ ID NO:2 or a fragment thereof. In a further embodiment the HERG polypeptide channel according to the invention has an amino acid sequence comprising the amino acid sequence of SEQ ID NO:2. In a preferred embodiment the HERG polypeptide according to the invention consists of SEQ ID NO:2.

Variants of the defined sequence and fragments also form part of the invention. Variants include those that vary from the parent sequence by conservative amino acid changes, wherein "conservative amino acid changes" refers to the replacement of one or more amino acid residue(s) in the parent sequence without affecting the biological activity of the parent molecule based on the art recognized substitutability of certain amino acids (See e.g. M. Dayhoff, *In Atlas of Protein Sequence and Structure*, Vol. 5, Supp. 3, pgs 345-352, 1987). Further variants are variants in which several, 5-10, 1-5, or 1-2 amino acids are substituted, deleted or added in any combination.

Methods for comparing the identity and similarity of two or more sequences are well known in the art. Thus for instance, programs available in the Wincosin Sequence Analysis Package, version 9.1 (Devreux J. et al, Nucleic Acid Res., 12, 387-395, 1984), for example the programs BESTFIT and GAP, may be used to determine the % identity between two polynucleotides and the % identity and the % similarity between two polypeptide sequences. BESTFIT uses the "local homology" algorithm of Smith and Waterman (J. Mol. Biol., 147, 195-197, 1981) and finds the best single region of similarity between two sequences. BESTFIT is more suited to compare two polynucleotide or two polypeptide sequences that are dissimilar in length, the program assuming that the shorter sequence represents a portion of the longer. In comparison, GAP aligns two sequences, finding a "maximum similarity", according to the algorithm of Neddleman and Wunsch (J. Mol. Biol., 48, 443-453, 1970). GAP is more suited to compare sequences that are approximately the same length and an alignment is expected over the entire length. Preferably, the parameters "Gap Weight" and "Length Weight" used in each program are 50 and 3 for polynucleotide sequences, and 12 and 4 for polypeptide sequences, respectively. Preferably, % identities and similarities are determined when the two sequences being compared are optimally aligned. Other programs for determining identity and/or similarity between sequences are also known in the art, for instance the BLAST family of programs (Altschul S F et al, Nucleic Acids Res., 25:3389-3402, 1997).

Those skilled in the art will recognize that the polypeptides according to the invention, i.e. the HERG polypeptide channel, could be obtained by a plurality of recombinant DNA techniques including, for example, hybridization, polymerase chain reaction (PCR) amplification, or de novo DNA synthesis (See e.g., T. Maniatis et al. *Molecular Cloning: A Laboratory Manual,* 2d Ed. Chap. 14 (1989)). Thus, in a further embodiment the present invention provides the use of the isolated and purified polynucleotides encoding the HERG polypeptide or a fragment thereof, in an assay or kit according to the invention. In another embodiment the present invention provides the use of the isolated and purified polynucleotide encoding the HERG polypeptide channel or a fragment thereof comprising the polynucleotide sequence of SEQ ID NO:1. In a preferred embodiment the present invention provides the use of the isolated and purified polynucleotide encoding the HERG polypeptide channel consisting of the polynuceotide sequence of SEQ ID NO:1.

The term "fragments thereof" describes a piece, or sub-region of protein or polynucleotide molecule whose sequence is disclosed herein, such that said fragment comprises 5 or more amino acids that are contiguous in the parent protein, or such that said fragment comprises 15 or more nucleic acids that are contiguous in the parent polynucleotide. The term "fragments thereof" is intended to include "functional fragments" wherein the isolated fragment, piece or sub-region comprises a functionally distinct region such as an active site, a binding site or a phosphorylation site of the receptor protein. Functional fragments may be produced by cloning technology, or as the natural products of alternative splicing techniques.

As used herein, "isolated" refers to the fact that the polynucleotides, proteins and polypeptides, or respective fragments thereof in question, have been removed from its in vivo environment so that it can be manipulated by the skilled artisan, such as but not limited to sequencing, restriction digestion, site-directed mutagenesis, and subcloning into expression vectors for a nucleic acid fragment as well as obtaining the protein or protein fragments in quantities that afford the opportunity to generate polyclonal antibodies, monoclonal antibodies, amino acid sequencing, and peptide digestion. Therefore, the nucleic acids as described herein can be present in whole cells or in cell lysates or in a partially, substantially or wholly purified form.

A polypeptide is considered "purified" when it is purified away from environmental contaminants. Thus a polypeptide isolated from cells is considered to be substantially purified when purified from cellular components by standard methods while a chemically synthesized polypeptide sequence is considered to be substantially purified when purified from its chemical precursors. A "substantially pure" protein or nucleic acid will typically comprise at least 85% of a sample with greater percentages being preferred. One method for determining the purity of a protein or nucleic acid molecule, is by electrophoresing a preparation in a matrix such as polyacrylamide or agarose. Purity is evidenced by the appearance of a single band after staining. Other methods for assessing purity include chromatography and analytical centrifugation.

The term "time sufficient to allow binding" as used herein refers to the time needed to generate a detectable amount of labeled reference compound bound to the HERG polypeptide channel. The time needed to generate this detectable amount will vary depending on the assay system. One of skill in the art will know the amount of time sufficient to generate a detectable amount of labeled reference compound bound to the HERG polypeptide channel based upon the assay system.

Assays

Assays of the present invention can be designed in many formats generally known in the art of screening compounds for binding polypeptide channels.

The assays of the present invention advantageously exploit the fact that the interaction of astemizole with the HERG potassium channel can be exploited to predict cardiotoxicity of compounds during the development of new therapeutics and other agents.

Therefore, the present invention provides an assay for screening test compounds, the assay comprising a) incubating a source containing HERG or a fragment thereof with; i)

a reference compound, ii) the test compound; and b) measuring the effect of the test compound on the amount of reference compound bound to HERG.

In a first embodiment of this invention the source containing HERG is an isolated and purified protein which encodes HERG having an amino acid sequence that is at least 80% identical to that of SEQ ID NO:2 or a fragment thereof.

In a second embodiment of this invention the source containing HERG is an isolated and purified protein which encodes HERG comprising the amino acid sequence of SEQ ID NO: 2 or a fragment thereof.

In a further embodiment of this invention the source containing HERG are cells expressing on the surface thereof the HERG polypeptide channel or a fragment thereof.

In another embodiment of this invention the source containing HERG are membrane preparations of cells expressing on the surface thereof the HERG polypeptide channel or a fragment thereof.

In an alternative embodiment of this invention, the reference compound is a compound capable to induce cardiotoxicity in a subject, preferably selected from the group consisting of astemizole, terfenadine, erythromycin, sparfloxain, probucol, terodiline and sertindole. In a preferred embodiment the reference compound is astemizole. It is a further object of this invention to provide assays wherein the reference compound is labeled, preferably radiolabeled.

In a preferred embodiment, the assay for screening test compounds for their capability to induce cardiotoxicity in a subject consists of a) incubating membrane preparations of cells expressing on the surface thereof HERG polypeptide channels encoded by the amino acid sequence consisting of SEQ ID NO:2 with i) [$^3$H]-astemizole, ii) the compound to be tested; and measuring the effect of the test compound on the amount of reference compound bound to HERG. The label of the reference compound is used to measure this effect wherein said label can be measured using amongst others scintillation counting.

A specific embodiment of the assays according to the invention, consists of an high-throughput assay for screening test compounds, the assay comprising: a) contacting membrane preparations of cells expressing on the surface thereof HERG polypeptide channels having an amino acid sequence that is at least 80% identical to that of SEQ ID NO:2 or fragments thereof, with a labeled reference compound for a time sufficient to allow binding of the reference compound with the HERG polypeptide channel; b) contacting membrane preparations of cells expressing on the surface thereof HERG polypeptide channels having an amino acid sequence that is at least 80% identical to that of SEQ ID NO:2 or fragments thereof, with the labeled reference compound of step a) together with the test compound for a time sufficient to allow binding of the reference compound and of the test compound with the HERG polypeptide channel; c) measuring the amount of labeled reference compound bound to the HERG channel in step a); d) measuring the amount of labeled reference compound bound to the HERG channel in step b); and e) compare the amount of labeled reference compound bound to the HERG channel measured in step a) with the amount of labeled reference compound bound to the HERG polypeptide channel measured in step b).

In a further embodiment the membrane preparations of the high-throughput screening assay consist of membrane preparations of cells expressing on the surface thereof the HERG polypeptide channel comprising the amino acid sequence of SEQ ID NO:2 or fragments thereof.

In a preferred embodiment of this invention the membrane preparations of the high-throughput screening assay consist of membrane preparations of cells, preferably HEK 293 cells, expressing on the surface thereof HERG polypeptide channels consisting of the amino acid sequence of SEQ ID NO:2.

In a further preferred embodiment, the labeled reference compound in the high-throughput screening assay consists of [$^3$H]-labeled astemizole. Said label can be measured using amongst others scintillation counting.

In another specific embodiment the present invention provides a high-throughput proximity detection assay for screening test compounds the assay comprising:
 i) HERG labeled with a first label capable of participating in a proximity detection assay;
 ii) a reference compound labeled with a second label capable of participating in a proximity detection assay;
 iii) contacting HERG of step i) and a reference compound of step ii) together with a test compound for a time sufficient to allow binding of the reference compound and of the test compound to HERG; and
 iv) detect an interaction between HERG of step i) and a reference compound of step ii) by means of proximity of the first label with the second label when HERG and the reference compound interact.

The proximity of the first label to the second label, brought about by the interaction of HERG and the reference compound results in the production of a detectable signal. This may be achieved by e.g. a scintillation proximity assay (SPA) system, in which one of the labels is a radiolabel suitable for use in SPA and the other label is a fluorescer comprised in a solid phase. The detectable signal is light energy emitted when the labeled HERG protein interacts with the labeled reference compound, bringing the radiolabel sufficiently close to the fluorescer. Scintillation proximity assay technology is described in U.S. Pat. No. 4,568,649.

Alternatively, the detectable signal may be a change in an existing signal output, eg. fluorescence. Fluorescence resonance energy transfer (FRET) is a method which works on this principle and is described by Tsien R. et al. (Tsien R. et al. (1993) Trends Cell Biol. 3: 242-245). It employs two different fluorescent molecules, a donor and an acceptor, such that when these are in sufficient proximity to one another the fluorescence of the donor molecule is absorbed by the acceptor molecule and light of another wavelength is emitted. Thus, when there is an interaction between two molecules such as HERG and a reference compound, each of which is labeled with one of these fluorescent molecules, a detectable signal is produced.

By such proximity assays as are described above, the screening assay according to the invention may be performed in a single step, i.e. without the need of a separation step to remove the excess of labeled reference compound from the incubation mixture using separation means such as filtration.

In a preferred embodiment of the high-throughput proximity detection assay, HERG is labeled with the fluorescer comprised in a solid phase, such as coated scintillation proximity assay beads and the reference compound is labeled with the radiolabel preferably the reference compound is radiolabeled astemizole of formula (III).

III

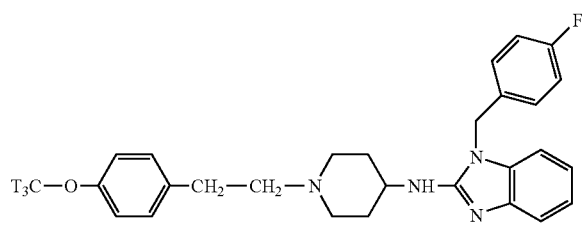

It will be readily appreciated by the skilled artisan that the binding of astemizole with HERG may also be used in a method for the structure-based or rational design of compound which affects the aforementioned binding, by:
  a) probing the structure of the binding site of the HERG polypeptide channel with astemizole;
  b) identifying contacting atoms in the binding site of the HERG polypeptide channel that interact with astemizole during binding;
  c) design test compounds that interact with the atoms identified in (b) to affect the HERG—astemizole interaction; and
  d) contact said designed test compound with a source containing HERG or a fragment thereof, to measure the capability of said compound to affect the amount of labeled astemizole bound to HERG.

It will be further appreciated that this will normally be an iterative process.

Kits

The present invention also provides kits that can be used in the above assays. In one embodiment the kit comprises a) a source containing HERG; b) a reference compound.

In a first embodiment the kit comprises a source containing HERG selected from: i) an isolated and purified protein which encodes HERG having an amino acid sequence that is at least 80% identical to that of SEQ ID NO:2 or a fragment thereof; ii) an isolated and purified protein which encodes HERG comprising the amino acid sequence of SEQ ID NO:2 or a fragment thereof; iii) cells expressing on the surface thereof the HERG polypeptide channel or a fragment thereof; or iv) membrane preparations of cells expressing on the surface thereof the HERG polypeptide channel or a fragment thereof.

In a further embodiment the kit comprises a reference compound is selected from the group consisting of astemizole, terfenadine, erythromycin, sparfloxain, probucol, terodiline and sertindole. In a preferred embodiment the reference compound is astemizole. It is a further object of this invention to provide kits wherein the reference compound is labeled, preferably radiolabeled.

In a specific embodiment the isolated and purified HERG polypeptide channel is bound to a solid support, preferably to a fluorescer comprising solid support such as coated scintillation proximity beads.

Thus, in a specific embodiment the kit comprises a) an isolated and purified HERG polypeptide channel or a fragment thereof, bound to a solid support; and b) a labeled reference compound. Preferably this specific embodiment consists of a kit comprising a) an isolated and purified HERG polypeptide channel consisting of the amino acid sequence of SEQ ID NO:2, bound to fluorescer comprising solid support; and b) a radiolabeled reference compound, preferably [$^3$H]-labeled astemizole.

In another specific embodiment the kit comprises a) membrane preparations of cells, preferably HEK293 cells, expressing on the surface thereof the HERG polypeptide channel consisting of the amino acid sequence of SEQ ID NO:2; b) [$^3$H]-labeled astemizole; and c) means for measurement of the amount of labeled reference compound bound to HERG.

The means of measurement consist of separating means to remove the excess of unbound labeled reference compound from the incubation mixture and of means for detection of the labeled reference compound. The person skilled in the art will know the separating means available for removing the excess of unbound labeled reference compound from the incubation mixture. Said separating means include, but are not limited to, magnetic beads, centrifugation techniques and filtration techniques. The means for detecting the labeled reference compound will be dependent on the labeled used. Said labels may be fluorescent or radiolabels. The skilled man will know the detection means available depending on the label used.

In a specific embodiment the separating means consists of GF/B filtration (Whatman Inc, Clifton, N.J.). In another specific embodiment the detection means consists of scintillation counting in a TOPCOUNT™(Packard, Meriden, CT).

In a further embodiment the kits of the invention further comprise instructions and/or multiple well plates for performing the assay.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXAMPLE 1

DNA Constructs and Stable Transfection of HEK293 Cells

HERG cDNA (Genbank Accession number: U04270 (SEQ ID NO:1)) was subcloned into bamHI/EcoRI sites of the pcDNA3 vector (Invitrogen). This vector contains a CMV promotor and a SV40 promotor, which drive the expression of the inserted cDNA (HERG) and neomycin resistance gene, respectively. The HEK293 cells were transfected with this construct by a calcium phosphate precipitate method (Gibco) or a lipofectamine method (Gibco). After selection in 800 μg/ml geneticin (G418; Gibco) for 15-20 days, single colonies were picked with cloning cylinders and tested for HERG current. The stably transfected cells were cultured in minimum essential medium (MEM) supplemented with 10% fetal bovine serum and 400 μg/ml geneticin.

For electrophysiological study, the cells were harvested from the culture dish by trypsinization, washed twice with standard MEM medium and seeded on small petri-dishes coated with poly-L-lysine. Experiments were performed on the cells 1-2 days after plating.

EXAMPLE 2

Membrane Preparations of HEK293 Cells Stably Transfected with the HERG Potassium Channel HEK293 cells stably transfected with the HERG channel cDNA, were grown in DMEM culture medium enriched with 10% fetal calf serum and antibiotics. Collected cells were homogenized in Tris-HCl 50 mM pH 7.4 using an Ultraturrax homogenizer and the homogenate was centrifuged for 10 min at 23,500×g in a SORVALL™ centrifuge. The cell membranes were washed once by re-homogenization and re-centrifugation. The membranes were suspended in Tris-HCl 50 mM pH 7.4, aliquoted and stored at −80 C.

EXAMPLE 3

Radiolabeling of Astemizole

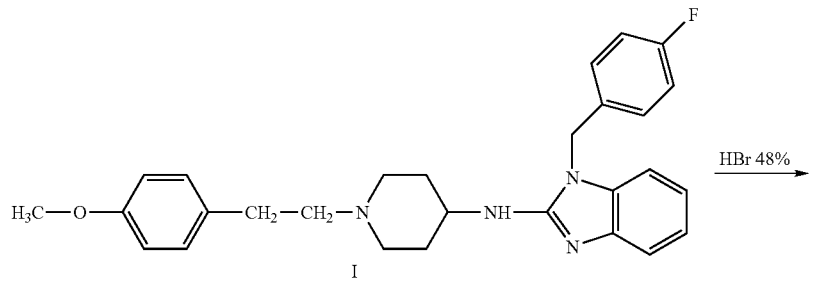

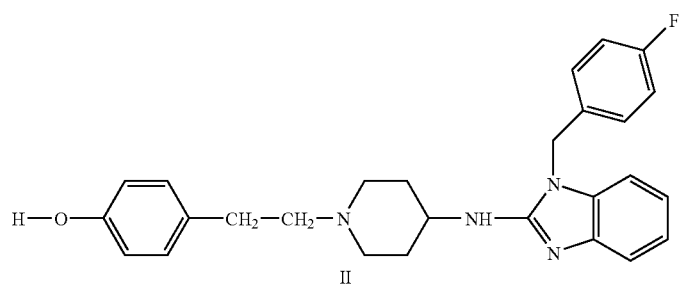

A solution of 4.6 g of astemizole (I) (10 mmol) in a 48% aqueous hydrobromic acid solution (80 ml) was stirred and refluxed for 2 hours. The reaction mixture was allowed to cool to room temperature and the formed precipitate was filtered and washed with water. The solids were dissolved in a mixture of N,N-dimethylformamide (20 ml) and water (20 ml) and the mixture was made alkaline by introducing slowly and with stirring a concentrated aqueous ammoniumhydroxide solution. Then water (100 ml) was added and the mixture was stirred for 1 h. The precipitate was filtered off and dried to the air for 18 h to yield desmethylastemizole (II).

From this amount a fraction was taken and thoroughly purified in portions via preparative HPLC on a Hypersyl ODS (5 μm) bonded phase stainless steel column (7.1 mm ID×300 mm) to yield astemizole free desmethylastemizole. Detection took place at 282 nm and elution was performed isocratically with acetonitrile-water-diisopropylamine (56:44:0.2, v/v) at a flow rate of 4.0 ml/min.

A fraction of the HPLC purified desmethylastemizole (II) (26.7 mg, 60 µmol) was dissolved in N,N-dimethylformamide (1.0 ml). To this solution 1N aqueous sodium hydroxide solution (60 µl, 60 µmol) was added. The mixture was stirred for 25 minutes at room temperature and added dropwise to a precooled solution (−78° C.) of [$^3$H]-methyliodide (370 MBq) in toluene. The reaction mixture was vortexed and then left without cooling for 3 hours. The toluene was evaporated from the reaction mixture on a waterbath of 40° C. at aspirator pressure and the residue was purified in portions via preparative HPLC as described above. The product containing fractions were combined and depleted to 70 ml with methanol to give [$^3$H]-astemizole (III) with a total radioactivity of 198 MBq and a specific activity of 3.14 TBq/mmol (85 Ci/mmol).

EXAMPLE 4

Radioligand Binding Assay

Membranes were thawed and re-homogenized in incubation buffer (Hepes 10 nM pH 7.4, 40 mM KCl, 20 mM $KH_2PO_4$, 5 mM $MgCl_2$, 0.5 mM $KHCO_3$, 10 mM glucose, 50 mM glutamate, 20 mM aspartate, 14 mM heptanoic acid, 1 mM EGTA, 0.1% BSA) and 20-100 µg protein was incubated with [$^3$H]-astemizole for 60 min at 25° C. with or without competitor followed by rapid filtration over GF/B filter using a Filtermate 196 harvester (Packard, Meriden, Conn.). Filters were rinsed extensively with ice-cold rinse-buffer (Tris-HCl 25 mM pH 7.4, 130 mM NaCl, 5.5 mM KCl, 5 mM glucose, 0.8 mM $MgCl_2$, 50 µM $CaCl_2$, 0.1% BSA). Filter bound radioactivity was determined by scintillation counting in a TOPCOUNT™ (Packard, Meriden, Conn.) and results were expressed as counts per minute (cpm).

Initially, various parameters including buffer, radioligand and compound to determined non-specific binding, were investigated in order to select the optimal conditions.

In a saturation binding experiment, increasing concentrations of [$^3$H]-astemizole were incubated with membranes, re-suspended in buffer. Non-specific binding was measured in the presence of 10 µM R66204 (FIG. 1).

The effect of BSA and/or cyclodextrine present in the incubation buffer, and of various ways of compound addition prior to the experiment, was investigated by comparing the binding affinities of 22 reference compounds to the electrophysiology data. Compounds were dissolved in DMSO and further diluted in the same solvent using a MULTIROBEIIυ pipetting station (Packard, Meriden, Conn.). The final DMSO concentration in all experiments was 1%. From this analysis it appears that compounds can be added directly from the DMSO stock solution. Attempts to increase the solubility of the compounds by addition of BSA and/or cyclodextrine did not improve the correlation significantly.

EXAMPLE 5

Whole-cell Voltage Clamp Technique (Patch Clamp)

Solutions: The bath solution contained (in mM) 150 NaCl, 4 KCl, 5 glucose, 10 HEPES, 1.8 $CaCl_2$ and 1 $MgCl_2$ (pH 7.4 with NaOH). The pipette solution contained (in mM) 120 KCl, 5 EGTA, 10 HEPES, 4 MgATP, 0.5 $CaCl_2$ and 2 $MgCl_2$ (pH 7.2 with KOH). Compounds were dissolved in DMSO to obtain a stock solution of $10^{-2}$M or $10^{-1}$M. Control (=bath solution+DMSO) and test solutions (=bath solution+DMSO+compound to be tested) contained 0.3%, 0.1% or 0.03% DMSO. Test and control solutions were applied to the cell under study using an Y-tube system, allowing to rapidly change solutions (less than 0.5 s) in the vicinity of the cell under study.

Electrophysiological measurements: A Petri dish containing attached HEK293 cells expressing HERG was fixed on the stage of a Patch Clamp Tower. An inverted microscope was used to observe the cells. The Petri dish was constantly perfused with the bath solution at room temperature.

Patch pipettes were pulled from borosilicate glass capillaries using a horizontal Flaming/Brown micropipette puller without further fire-polishing. The microelectrodes used had an input resistance between 1.5 and 3 MΩ when filled with the pipette solution.

The membrane current of the cells was measured at distinct membrane potentials with the patch clamp technique by means of an EPC-9 patch clamp amplifier. Data were acquired and analysed using the programs Pulse and Pulsefit (HEKA), DataAccess (Bruxton) and Igor (Wavemetrics). The current signals were low-pass filtered and subsequently digitised. The liquid junction potential was electronically corrected, before establishing the seal. After disruption of the membrane, the cell capacitance and the series resistance were compensated using the circuit of the EPC-9 patch clamp amplifier.

The holding potential was −80 mV. The HERG current ($K^+$-selective outward current) was determined as the maximal tail current at −40 mV after a 2 second depolarization to +60 mV. Pulse cycling rate was 15 s. Before each test pulse a short pulse (0.5 s) from the holding potential to −60 mV was given to determine leak current. After establishing whole-cell configuration a 5 minute equilibration period allowed for internal perfusion of the cell with the pipette solution. Thereafter test pulses were given for 5 minutes to quantify the HERG current under control conditions. While continuing the pulse protocol, perfusion was switched from control solution to drug-containing solution. The effect of the drug was measured after 5 minutes of drug application. One to three concentrations of the drug were tested per cell (applied cumulatively).

Parameter analysis of the measurements: The HERG current was determined as the maximal tail current at −40 mV after a 2 second depolarization to +60 mV, starting from a holding potential of −80 mV.

During the initial 5 minutes measured in the presence of the control solution, the amplitude of the HERG-mediated membrane $K^+$ current gradually decreased with time (run-down). In order to quantify accurately the extent of block by the compounds, this continuous run-down of the $K^+$ current has to be taken into account. Therefore the time course of the $K^+$ current (measured at −40 mV) was fitted exponentially to the initial period of 5 minutes in control solution and extrapolated for the remainder of the experiment. These extrapolations give the estimated amplitude of the current if no drug would have been given. To determine the extent of block by the compounds, the ratio of the measured current was calculated by dividing each measured current amplitude by the value of the fitted current at the same point in time.

EXAMPLE 6

Pharmacological Evaluation of the Binding Assay

For the pharmacological evaluation of the binding assay, 322 compounds were tested at 8 concentrations, for their ability to inhibit [$^3$H]-astemizole binding to the HERG channel and $pIC_{50}$-values were calculated by non-linear regression analysis. If pIC$_{50}$ values were available, the rank order (Spearman) of the potencies for binding and patch clamp was compared.

Figure 2:
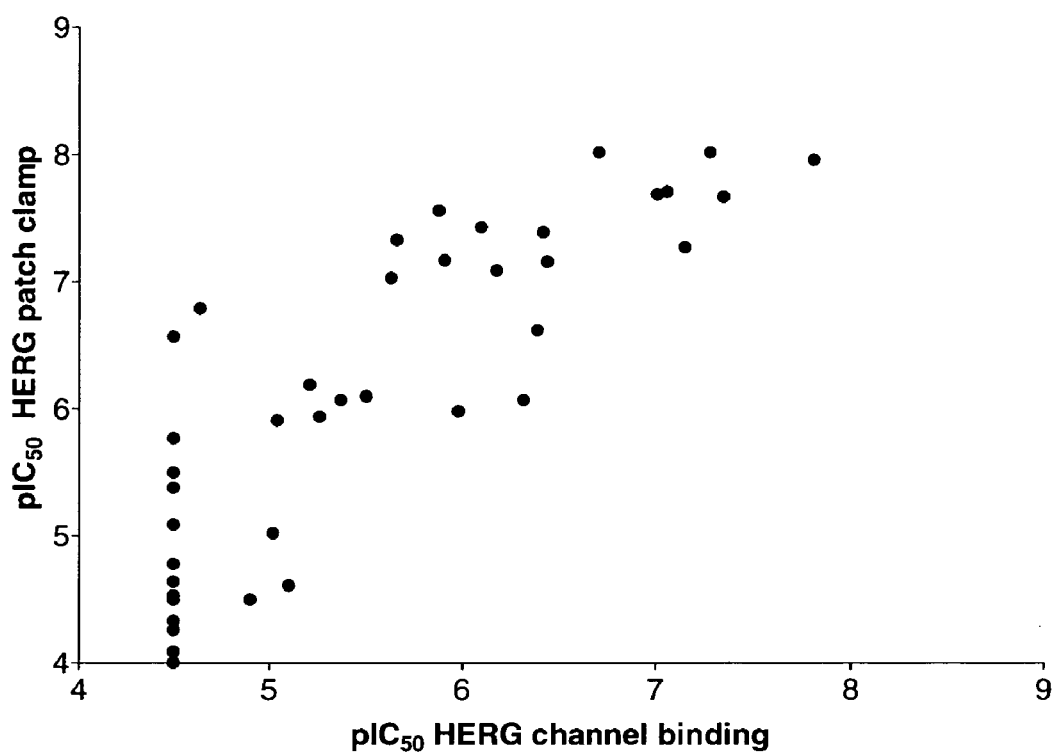
FIG. 2 shows the binding affinities of 42 reference compounds compared to the electrophysiological patch clamp data. A Spearman rank correlation coefficient of 0.87 could be obtained.

If in the patch clamp assay, compounds only have been tested at <4 concentrations, a score was assigned to both binding and patch clamp data according to the following criteria:

score 1: pIC50<6 or % blockade<50% at $10^{-6}$M or higher
score 2: pIC50 between 6-8 or % blockade<50% between $10^{-6}$ and $10^{-8}$M
score 3: pIC50>8 or % blockade>50% at $10^{-8}$M or lower The rank order of potencies of 42 reference compounds to displace the [$^3$H]-astemizole binding from the HERG channel, correlates well with the electrophysiological data for the functional blockade of the rapid activating delayed rectifier K$^+$ current ($r_{SP}$=0.87) (FIG. 2).

For 94% of the compounds tested, the binding data correlate with the patch clamp data. In 2% of the cases the binding assay scored higher than the patch clamp assay, for the remaining 4% it is the other way around, i.e. the patch clamp assay scores higher than the binding assay.

In view of this good correlation between binding data and electrophysiological data it may be concluded that the radio-ligand binding assay can be used as a primary screening tool for the prediction of potential cardiovascular side-effects.

The invention claimed is:

1. An assay for screening test compounds, comprising:
a) incubating a source containing a HERG polypeptide comprising SEQ ID NO: 2 with:
i) radiolabeled astemizole of formula (III)

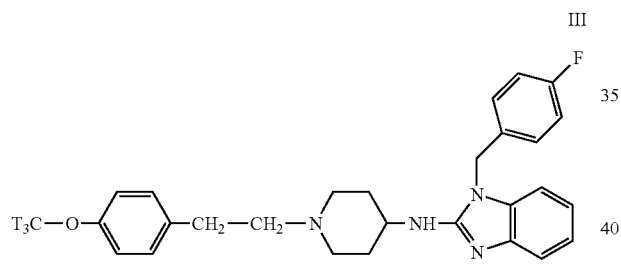

III b) incubating the source containing a HERG polypeptide comprising SEQ ID NO: 2 and the radiolabeled astemizole of formula III with:
ii) the test compound;
c) measuring the amount of radiolabeled astemizole bound to the HERG polypeptide in step a);
d) measuring the amount of radiolabeled astemizole bound to the HERG polypeptide in step b);
e) comparing the amount of radiolabeled astemizole bound to the HERG polypeptide measured in step a) with the amount of radiolabeled astemizole bound to the HERG polypeptide measured in step b);
wherein a decrease in the amount of radiolabeled astemizole bound as a result of said test compound indicates that said test compound may induce cardiotoxicity or cardiac arrythmia in a subject.

2. The assay of claim 1, wherein said assay is a high-throughput assay.

3. The assay of claim 2, wherein said assay is a high-throughput proximity detection assay.

4. An assay according to claim 1, wherein the source containing said HERG polypeptide is selected from the group consisting of:

i) cells expressing on the surface thereof a HERG polypeptide comprising SEQ ID NO: 2; or
ii) membrane preparations of cells expressing on the surface thereof the HERG polypeptide comprising SEQ ID NO: 2.

5. An assay for screening test compounds, comprising:
a) incubating a source containing membrane preparations of cells expressing on the surface thereof the HERG polypeptide consisting of SEQ ID NO:2 with:
i) radiolabeled astemizole of formula (III)

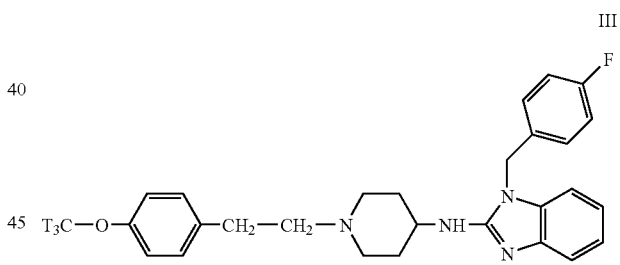

III b) incubating the source containing a HERG polypeptide and the radiolabeled astemizole of formula III with:
ii) the test compound;
c) measuring the amount of radiolabeled astemizole bound to the HERG polypeptide in step a);
d) measuring the amount of radiolabeled astemizole bound to the HERG polypeptide in step b);
e) comparing the amount of radiolabeled astemizole bound to the HERG polypeptide measured in step a) with the amount of radiolabeled astemizole bound to the HERG polypeptide measured in step b);
wherein a decrease in the amount of radiolabeled astemizole bound as a result of said test compound indicates that said test compound may induce cardiotoxicity or cardiac arrhythmia in a subject.

* * * * *

SEQUENCE LISTING

```
<160> NUMBER OF SEQ ID NOS: 2

<210> SEQ ID NO 1
<211> LENGTH: 4070
<212> TYPE: DNA
<213> ORGANISM: Homo sapiens
<220> FEATURE:
<221> NAME/KEY: CDS
<222> LOCATION: (184)..(3663)
<300> PUBLICATION INFORMATION:
<301> AUTHORS: Warmke, J. W.
<302> TITLE: Human putative potassium channel subunit (h-erg) mRNA,
       complete cds.
<308> DATABASE ACCESSION NUMBER: GenBank / U04270
<309> DATABASE ENTRY DATE: 1993-12-09
<313> RELEVANT RESIDUES: 1 TO 4070

<400> SEQUENCE: 1
acgcggcctg ctcaggcctc cagcggccgg tcggagggga ggcgggaggc gagcgaggac      60
ccgcgcccgc agtccagtct gtgcgcgccc gtgctcgctt ggcgcggtgc gggaccagcg     120
ccggccaccc gaagcctagt gcgtcgccgg gtgggtgggc ccgcccggcg ccatgggctc     180 agg atg ccg gtg cgg agg ggc cac gtc gcg ccg cag aac acc ttc ctg       228
    Met Pro Val Arg Arg Gly His Val Ala Pro Gln Asn Thr Phe Leu
    1               5                   10                  15 gac acc atc atc cgc aag ttt gag ggc cag agc cgt aag ttc atc atc       276
Asp Thr Ile Ile Arg Lys Phe Glu Gly Gln Ser Arg Lys Phe Ile Ile
                20                  25                  30 gcc aac gct cgg gtg gag aac tgc gcc gtc atc tac tgc aac gac ggc       324
Ala Asn Ala Arg Val Glu Asn Cys Ala Val Ile Tyr Cys Asn Asp Gly
            35                  40                  45 ttc tgc gag ctg tgc ggc tac tcg cgg gcc gag gtg atg cag cga ccc       372
Phe Cys Glu Leu Cys Gly Tyr Ser Arg Ala Glu Val Met Gln Arg Pro
        50                  55                  60 tgc acc tgc gac ttc ctg cac ggg ccg cgc acg cag cgc cgc gct gcc       420
Cys Thr Cys Asp Phe Leu His Gly Pro Arg Thr Gln Arg Arg Ala Ala
    65                  70                  75 gcg cag atc gcg cag gca ctg ctg ggc gcc gag gag cgc aaa gtg gaa       468
Ala Gln Ile Ala Gln Ala Leu Leu Gly Ala Glu Glu Arg Lys Val Glu
80                  85                  90                  95 atc gcc ttc tac cgg aaa gat ggg agc tgc ttc cta tgt ctg gtg gat       516
Ile Ala Phe Tyr Arg Lys Asp Gly Ser Cys Phe Leu Cys Leu Val Asp
                100                 105                 110 gtg gtg ccc gtg aag aac gag gat ggg gct gtc atc atg ttc atc ctc       564
Val Val Pro Val Lys Asn Glu Asp Gly Ala Val Ile Met Phe Ile Leu
            115                 120                 125 aat ttc gag gtg gtg atg gag aag gac atg gtg ggg tcc ccg gct cat       612
Asn Phe Glu Val Val Met Glu Lys Asp Met Val Gly Ser Pro Ala His
```

-continued

|  |  |  |  |  |  |  |  |  |  |  |  |  |  |  |  |  |
|---|---|---|---|---|---|---|---|---|---|---|---|---|---|---|---|---|
|  |  | 130 |  |  |  | 135 |  |  |  | 140 |  |  |  |  |  |  |
| gac | acc | aac | cac | cgg | ggc | ccc | ccc | acc | agc | tgg | ctg | gcc | cca | ggc | cgc | 660 |
| Asp | Thr | Asn | His | Arg | Gly | Pro | Pro | Thr | Ser | Trp | Leu | Ala | Pro | Gly | Arg |  |
|  | 145 |  |  |  | 150 |  |  |  |  | 155 |  |  |  |  |  |  |
| gcc | aag | acc | ttc | cgc | ctg | aag | ctg | ccc | gcg | ctg | ctg | gcg | ctg | acg | gcc | 708 |
| Ala | Lys | Thr | Phe | Arg | Leu | Lys | Leu | Pro | Ala | Leu | Leu | Ala | Leu | Thr | Ala |  |
| 160 |  |  |  |  | 165 |  |  |  | 170 |  |  |  |  |  | 175 |  |
| cgg | gag | tcg | tcg | gtg | cgg | tcg | ggc | ggc | gcg | ggc | ggc | gcg | ggc | gcc | ccg | 756 |
| Arg | Glu | Ser | Ser | Val | Arg | Ser | Gly | Gly | Ala | Gly | Gly | Ala | Gly | Ala | Pro |  |
|  |  |  |  | 180 |  |  |  |  | 185 |  |  |  |  | 190 |  |  |
| ggg | gcc | gtg | gtg | gtg | gac | gtg | gac | ctg | acg | ccc | gcg | gca | ccc | agc | agc | 804 |
| Gly | Ala | Val | Val | Val | Asp | Val | Asp | Leu | Thr | Pro | Ala | Ala | Pro | Ser | Ser |  |
|  |  |  | 195 |  |  |  |  | 200 |  |  |  |  | 205 |  |  |  |
| gag | tcg | ctg | gcc | ctg | gac | gaa | gtg | aca | gcc | atg | gac | aac | cac | gtg | gca | 852 |
| Glu | Ser | Leu | Ala | Leu | Asp | Glu | Val | Thr | Ala | Met | Asp | Asn | His | Val | Ala |  |
|  |  |  | 210 |  |  |  |  | 215 |  |  |  |  | 220 |  |  |  |
| ggg | ctc | ggg | ccc | gcg | gag | gag | cgg | cgt | gcg | ctg | gtg | ggt | ccc | ggc | tct | 900 |
| Gly | Leu | Gly | Pro | Ala | Glu | Glu | Arg | Arg | Ala | Leu | Val | Gly | Pro | Gly | Ser |  |
| 225 |  |  |  |  | 230 |  |  |  |  | 235 |  |  |  |  |  |  |
| ccg | ccc | cgc | agc | gcg | ccc | ggc | cag | ctc | cca | tcg | ccc | cgg | gcg | cac | agc | 948 |
| Pro | Pro | Arg | Ser | Ala | Pro | Gly | Gln | Leu | Pro | Ser | Pro | Arg | Ala | His | Ser |  |
| 240 |  |  |  |  | 245 |  |  |  |  | 250 |  |  |  |  | 255 |  |
| ctc | aac | ccc | gac | gcc | tcg | ggc | tcc | agc | tgc | agc | ctg | gcc | cgg | acg | cgc | 996 |
| Leu | Asn | Pro | Asp | Ala | Ser | Gly | Ser | Ser | Cys | Ser | Leu | Ala | Arg | Thr | Arg |  |
|  |  |  | 260 |  |  |  |  | 265 |  |  |  |  | 270 |  |  |  |
| tcc | cga | gaa | agc | tgc | gcc | agc | gtg | cgc | cgc | gcc | tcg | tcg | gcc | gac | gac | 1044 |
| Ser | Arg | Glu | Ser | Cys | Ala | Ser | Val | Arg | Arg | Ala | Ser | Ser | Ala | Asp | Asp |  |
|  |  | 275 |  |  |  |  | 280 |  |  |  |  | 285 |  |  |  |  |
| atc | gag | gcc | atg | cgc | gcc | ggg | gtg | ctg | ccc | ccg | cca | ccg | cgc | cac | gcc | 1092 |
| Ile | Glu | Ala | Met | Arg | Ala | Gly | Val | Leu | Pro | Pro | Pro | Pro | Arg | His | Ala |  |
|  |  | 290 |  |  |  |  | 295 |  |  |  |  | 300 |  |  |  |  |
| agc | acc | ggg | gcc | atg | cac | cca | ctg | cgc | agc | ggc | ttg | ctc | aac | tcc | acc | 1140 |
| Ser | Thr | Gly | Ala | Met | His | Pro | Leu | Arg | Ser | Gly | Leu | Leu | Asn | Ser | Thr |  |
| 305 |  |  |  |  | 310 |  |  |  |  | 315 |  |  |  |  |  |  |
| tcg | gac | tcc | gac | ctc | gtg | cgc | tac | cgc | acc | att | agc | aag | att | ccc | caa | 1188 |
| Ser | Asp | Ser | Asp | Leu | Val | Arg | Tyr | Arg | Thr | Ile | Ser | Lys | Ile | Pro | Gln |  |
| 320 |  |  |  |  | 325 |  |  |  |  | 330 |  |  |  |  | 335 |  |
| atc | acc | ctc | aac | ttt | gtg | gac | ctc | aag | ggc | gac | ccc | ttc | ttg | gct | tcg | 1236 |
| Ile | Thr | Leu | Asn | Phe | Val | Asp | Leu | Lys | Gly | Asp | Pro | Phe | Leu | Ala | Ser |  |
|  |  |  |  | 340 |  |  |  |  | 345 |  |  |  |  | 350 |  |  |
| ccc | acc | agt | gac | cgt | gag | atc | ata | gca | cct | aag | ata | aag | gag | cga | acc | 1284 |
| Pro | Thr | Ser | Asp | Arg | Glu | Ile | Ile | Ala | Pro | Lys | Ile | Lys | Glu | Arg | Thr |  |
|  |  | 355 |  |  |  |  | 360 |  |  |  |  | 365 |  |  |  |  |
| cac | aat | gtc | act | gag | aag | gtc | acc | cag | gtc | ctg | tcc | ctg | ggc | gcc | gac | 1332 |
| His | Asn | Val | Thr | Glu | Lys | Val | Thr | Gln | Val | Leu | Ser | Leu | Gly | Ala | Asp |  |
|  |  | 370 |  |  |  |  | 375 |  |  |  |  | 380 |  |  |  |  |
| gtg | ctg | cct | gag | tac | aag | ctg | cag | gca | ccg | cgc | atc | cac | cgc | tgg | acc | 1380 |
| Val | Leu | Pro | Glu | Tyr | Lys | Leu | Gln | Ala | Pro | Arg | Ile | His | Arg | Trp | Thr |  |
| 385 |  |  |  |  | 390 |  |  |  |  | 395 |  |  |  |  |  |  |
| atc | ctg | cat | tac | agc | ccc | ttc | aag | gcc | gtg | tgg | gac | tgg | ctc | atc | ctg | 1428 |
| Ile | Leu | His | Tyr | Ser | Pro | Phe | Lys | Ala | Val | Trp | Asp | Trp | Leu | Ile | Leu |  |
| 400 |  |  |  |  | 405 |  |  |  |  | 410 |  |  |  |  | 415 |  |
| ctg | ctg | gtc | atc | tac | acg | gct | gtc | ttc | aca | ccc | tac | tcg | gct | gcc | ttc | 1476 |
| Leu | Leu | Val | Ile | Tyr | Thr | Ala | Val | Phe | Thr | Pro | Tyr | Ser | Ala | Ala | Phe |  |
|  |  |  |  | 420 |  |  |  |  | 425 |  |  |  |  | 430 |  |  |
| ctg | ctg | aag | gag | acg | gaa | gaa | ggc | ccg | cct | gct | acc | gag | tgt | ggc | tac | 1524 |
| Leu | Leu | Lys | Glu | Thr | Glu | Glu | Gly | Pro | Pro | Ala | Thr | Glu | Cys | Gly | Tyr |  |
|  |  | 435 |  |  |  |  | 440 |  |  |  |  | 445 |  |  |  |  |
| gcc | tgc | cag | ccg | ctg | gct | gtg | gtg | gac | ctc | atc | gtg | gac | atc | atg | ttc | 1572 |

```
                Ala Cys Gln Pro Leu Ala Val Val Asp Leu Ile Val Asp Ile Met Phe
                        450                 455                 460 att gtg gac atc ctc atc aac ttc cgc acc acc tac gtc aat gcc aac                1620
Ile Val Asp Ile Leu Ile Asn Phe Arg Thr Thr Tyr Val Asn Ala Asn
        465                 470                 475 gag gag gtg gtc agc cac ccc ggc cgc atc gcc gtc cac tac ttc aag                1668
Glu Glu Val Val Ser His Pro Gly Arg Ile Ala Val His Tyr Phe Lys
480                 485                 490                 495 ggc tgg ttc ctc atc gac atg gtg gcc gcc atc ccc ttc gac ctg ctc                1716
Gly Trp Phe Leu Ile Asp Met Val Ala Ala Ile Pro Phe Asp Leu Leu
                500                 505                 510 atc ttc ggc tct ggc tct gag gag ctg atc ggg ctg ctg aag act gcg                1764
Ile Phe Gly Ser Gly Ser Glu Glu Leu Ile Gly Leu Leu Lys Thr Ala
                    515                 520                 525 cgg ctg ctg cgg ctg gtg cgc gtg gcg cgg aag ctg gat cgc tac tca                1812
Arg Leu Leu Arg Leu Val Arg Val Ala Arg Lys Leu Asp Arg Tyr Ser
            530                 535                 540 gag tac ggc gcg gcc gtg ctg ttc ttg ctc atg tgc acc ttt gcg ctc                1860
Glu Tyr Gly Ala Ala Val Leu Phe Leu Leu Met Cys Thr Phe Ala Leu
        545                 550                 555 atc gcg cac tgg cta gcc tgc atc tgg tac gcc atc ggc aac atg gag                1908
Ile Ala His Trp Leu Ala Cys Ile Trp Tyr Ala Ile Gly Asn Met Glu
560                 565                 570                 575 cag cca cac atg gac tca cgc atc ggc tgg ctg cac aac ctg ggc gac                1956
Gln Pro His Met Asp Ser Arg Ile Gly Trp Leu His Asn Leu Gly Asp
                580                 585                 590 cag ata ggc aaa ccc tac aac agc agc ggc ctg ggc ggc ccc tcc atc                2004
Gln Ile Gly Lys Pro Tyr Asn Ser Ser Gly Leu Gly Gly Pro Ser Ile
                    595                 600                 605 aag gac aag tat gtg acg gcg ctc tac ttc acc ttc agc agc ctc acc                2052
Lys Asp Lys Tyr Val Thr Ala Leu Tyr Phe Thr Phe Ser Ser Leu Thr
            610                 615                 620 agt gtg ggc ttc ggc aac gtc tct ccc aac acc aac tca gag aag atc                2100
Ser Val Gly Phe Gly Asn Val Ser Pro Asn Thr Asn Ser Glu Lys Ile
        625                 630                 635 ttc tcc atc tgc gtc atg ctc att ggc tcc ctc atg tat gct agc atc                2148
Phe Ser Ile Cys Val Met Leu Ile Gly Ser Leu Met Tyr Ala Ser Ile
640                 645                 650                 655 ttc ggc aac gtg tcg gcc atc atc cag cgg ctg tac tcg ggc aca gcc                2196
Phe Gly Asn Val Ser Ala Ile Ile Gln Arg Leu Tyr Ser Gly Thr Ala
                660                 665                 670 cgc tac cac aca cag atg ctg cgg gtg cgg gag ttc atc cgc ttc cac                2244
Arg Tyr His Thr Gln Met Leu Arg Val Arg Glu Phe Ile Arg Phe His
                    675                 680                 685 cag atc ccc aat ccc ctg cgc cag cgc ctc gag gag tac ttc cag cac                2292
Gln Ile Pro Asn Pro Leu Arg Gln Arg Leu Glu Glu Tyr Phe Gln His
            690                 695                 700 gcc tgg tcc tac acc aac ggc atc gac atg aac gcg gtg ctg aag ggc                2340
Ala Trp Ser Tyr Thr Asn Gly Ile Asp Met Asn Ala Val Leu Lys Gly
        705                 710                 715 ttc cct gag tgc ctg cag gct gac atc tgc ctg cac ctg aac cgc tca                2388
Phe Pro Glu Cys Leu Gln Ala Asp Ile Cys Leu His Leu Asn Arg Ser
720                 725                 730                 735 ctg ctg cag cac tgc aaa ccc ttc cga ggg gcc acc aag ggc tgc ctt                2436
Leu Leu Gln His Cys Lys Pro Phe Arg Gly Ala Thr Lys Gly Cys Leu
                740                 745                 750 cgg gcc ctg gcc atg aag ttc aag acc aca cat gca ccg cca ggg gac                2484
Arg Ala Leu Ala Met Lys Phe Lys Thr Thr His Ala Pro Pro Gly Asp
                    755                 760                 765
```

```
aca ctg gtg cat gct ggg gac ctg ctc acc gcc ctg tac ttc atc tcc     2532
Thr Leu Val His Ala Gly Asp Leu Leu Thr Ala Leu Tyr Phe Ile Ser
            770                 775                 780 cgg ggc tcc atc gag atc ctg cgg ggc gac gtc gtc gtg gcc atc ctg     2580
Arg Gly Ser Ile Glu Ile Leu Arg Gly Asp Val Val Val Ala Ile Leu
        785                 790                 795 ggg aag aat gac atc ttt ggg gag cct ctg aac ctg tat gca agg cct     2628
Gly Lys Asn Asp Ile Phe Gly Glu Pro Leu Asn Leu Tyr Ala Arg Pro
800                 805                 810                 815 ggc aag tcg aac ggg gat gtg cgg gcc ctc acc tac tgt gac cta cac     2676
Gly Lys Ser Asn Gly Asp Val Arg Ala Leu Thr Tyr Cys Asp Leu His
                820                 825                 830 aag atc cat cgg gac gac ctg ctg gag gtg ctg gac atg tac cct gag     2724
Lys Ile His Arg Asp Asp Leu Leu Glu Val Leu Asp Met Tyr Pro Glu
            835                 840                 845 ttc tcc gac cac ttc tgg tcc agc ctg gag atc acc ttc aac ctg cga     2772
Phe Ser Asp His Phe Trp Ser Ser Leu Glu Ile Thr Phe Asn Leu Arg
        850                 855                 860 gat acc aac atg atc ccg ggc tcc ccc ggc agt acg gag tta gag ggt     2820
Asp Thr Asn Met Ile Pro Gly Ser Pro Gly Ser Thr Glu Leu Glu Gly
865                 870                 875 ggc ttc agt cgg caa cgc aag cgc aag ttg tcc ttc cgc agg cgc acg     2868
Gly Phe Ser Arg Gln Arg Lys Arg Lys Leu Ser Phe Arg Arg Arg Thr
880                 885                 890                 895 gac aag gac acg gag cag cca ggg gag gtg tcg gcc ttg ggg ccg ggc     2916
Asp Lys Asp Thr Glu Gln Pro Gly Glu Val Ser Ala Leu Gly Pro Gly
                900                 905                 910 cgg gcg ggg gca ggg ccg agt agc cgg ggc cgg ccg ggg ggg ccg tgg     2964
Arg Ala Gly Ala Gly Pro Ser Ser Arg Gly Arg Pro Gly Gly Pro Trp
            915                 920                 925 ggg gag agc ccg tcc agt ggc ccc tcc agc cct gag agc agt gag gat     3012
Gly Glu Ser Pro Ser Ser Gly Pro Ser Ser Pro Glu Ser Ser Glu Asp
        930                 935                 940 gag ggc cca ggc cgc agc tcc agc ccc ctc cgc ctg gtg ccc ttc tcc     3060
Glu Gly Pro Gly Arg Ser Ser Ser Pro Leu Arg Leu Val Pro Phe Ser
945                 950                 955 agc ccc agg ccc ccc gga gag ccg ccg ggt ggg gag ccc ctg atg gag     3108
Ser Pro Arg Pro Pro Gly Glu Pro Pro Gly Gly Glu Pro Leu Met Glu
                960                 965                 970                 975 gac tgc gag aag agc agc gac act tgc aac ccc ctg tca ggc gcc ttc     3156
Asp Cys Glu Lys Ser Ser Asp Thr Cys Asn Pro Leu Ser Gly Ala Phe
            980                 985                 990 tca gga gtg tcc aac att ttc agc ttc tgg ggg gac agt cgg ggc cgc     3204
Ser Gly Val Ser Asn Ile Phe Ser Phe Trp Gly Asp Ser Arg Gly Arg
        995                 1000                1005 cag tac cag gag ctc cct cga tgc ccc gcc ccc acc ccc agc ctc ctc     3252
Gln Tyr Gln Glu Leu Pro Arg Cys Pro Ala Pro Thr Pro Ser Leu Leu
        1010                1015                1020 aac atc ccc ctc tcc agc ccg ggt cgg cgg ccc cgg ggc gac gtg gag     3300
Asn Ile Pro Leu Ser Ser Pro Gly Arg Arg Pro Arg Gly Asp Val Glu
        1025                1030                1035 agc agg ctg gat gcc ctc cag cgc cag ctc aac agg ctg gag acc cgg     3348
Ser Arg Leu Asp Ala Leu Gln Arg Gln Leu Asn Arg Leu Glu Thr Arg
        1040                1045                1050                1055 ctg agt gca gac atg gcc act gtc ctg cag ctg cta cag agg cag atg     3396
Leu Ser Ala Asp Met Ala Thr Val Leu Gln Leu Leu Gln Arg Gln Met
                1060                1065                1070 acg ctg gtc ccg ccc gcc tac agt gct gtg acc acc ccg ggg cct ggc     3444
Thr Leu Val Pro Pro Ala Tyr Ser Ala Val Thr Thr Pro Gly Pro Gly
            1075                1080                1085
```

```
                                                            -continued
ccc act tcc aca tcc ccg ctg ttg ccc gtc agc ccc ctc ccc acc ctc         3492
Pro Thr Ser Thr Ser Pro Leu Leu Pro Val Ser Pro Leu Pro Thr Leu
    1090                1095                1100 acc ttg gac tcg ctt tct cag gtt tcc cag ttc atg gcg tgt gag gag         3540
Thr Leu Asp Ser Leu Ser Gln Val Ser Gln Phe Met Ala Cys Glu Glu
1105                1110                1115 ctg ccc ccg ggg gcc cca gag ctt ccc caa gaa ggc ccc aca cga cgc         3588
Leu Pro Pro Gly Ala Pro Glu Leu Pro Gln Glu Gly Pro Thr Arg Arg
1120                1125                1130                1135 ctc tcc cta ccg ggc cag ctg ggg gcc ctc acc tcc cag ccc ctg cac         3636
Leu Ser Leu Pro Gly Gln Leu Gly Ala Leu Thr Ser Gln Pro Leu His
            1140                1145                1150 aga cac ggc tcg gac ccg ggc agt tag tggggctgcc cagtgtggac               3683
Arg His Gly Ser Asp Pro Gly Ser
        1155                1160 acgtggctca cccagggatc aaggcgctgc tgggccgctc cccttggagg ccctgctcag       3743
gaggccctga ccgtggaagg ggagaggaac tcgaaagcac agctcctccc ccagcccttg       3803
ggaccatctt ctcctgcagt cccctgggcc ccagtgagag gggcaggggc agggccggca       3863
gtaggtgggg cctgtggtcc ccccactgcc ctgagggcat tagctggtct aactgcccgg       3923
aggcacccgg ccctgggcct taggcacctc aaggactttt ctgctattta ctgctcttat       3983
tgttaaggat aataattaag gatcatatga ataattaatg aagatgctga tgactatgaa       4043
taataaataa ttatcctgag gagaaaa                                           4070

<210> SEQ ID NO 2
<211> LENGTH: 1159
<212> TYPE: PRT
<213> ORGANISM: Homo sapiens

<400> SEQUENCE: 2

Met Pro Val Arg Arg Gly His Val Ala Pro Gln Asn Thr Phe Leu Asp
 1               5                  10                  15

Thr Ile Ile Arg Lys Phe Glu Gly Gln Ser Arg Lys Phe Ile Ile Ala
                20                  25                  30

Asn Ala Arg Val Glu Asn Cys Ala Val Ile Tyr Cys Asn Asp Gly Phe
            35                  40                  45

Cys Glu Leu Cys Gly Tyr Ser Arg Ala Glu Val Met Gln Arg Pro Cys
        50                  55                  60

Thr Cys Asp Phe Leu His Gly Pro Arg Thr Gln Arg Arg Ala Ala Ala
65                  70                  75                  80

Gln Ile Ala Gln Ala Leu Leu Gly Ala Glu Glu Arg Lys Val Glu Ile
                85                  90                  95

Ala Phe Tyr Arg Lys Asp Gly Ser Cys Phe Leu Cys Leu Val Asp Val
                100                 105                 110

Val Pro Val Lys Asn Glu Asp Gly Ala Val Ile Met Phe Ile Leu Asn
            115                 120                 125

Phe Glu Val Val Met Glu Lys Asp Met Val Gly Ser Pro Ala His Asp
        130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Gly Ala Gly Gly Ala Gly Ala Pro Gly
                180                 185                 190
```

-continued

```
Ala Val Val Val Asp Val Asp Leu Thr Pro Ala Ala Pro Ser Ser Glu
            195                 200                 205

Ser Leu Ala Leu Asp Glu Val Thr Ala Met Asp Asn His Val Ala Gly
        210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Ala Ser Ser Ala Asp Asp Ile
        275                 280                 285

Glu Ala Met Arg Ala Gly Val Leu Pro Pro Pro Arg His Ala Ser
290                 295                 300

Thr Gly Ala Met His Pro Leu Arg Ser Gly Leu Leu Asn Ser Thr Ser
305                 310                 315                 320

Asp Ser Asp Leu Val Arg Tyr Arg Thr Ile Ser Lys Ile Pro Gln Ile
                325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
        355                 360                 365

Asn Val Thr Glu Lys Val Thr Gln Val Leu Ser Leu Gly Ala Asp Val
    370                 375                 380

Leu Pro Glu Tyr Lys Leu Gln Ala Pro Arg Ile His Arg Trp Thr Ile
385                 390                 395                 400

Leu His Tyr Ser Pro Phe Lys Ala Val Trp Asp Trp Leu Ile Leu Leu
                405                 410                 415

Leu Val Ile Tyr Thr Ala Val Phe Thr Pro Tyr Ser Ala Ala Phe Leu
            420                 425                 430

Leu Lys Glu Thr Glu Glu Gly Pro Pro Ala Thr Glu Cys Gly Tyr Ala
        435                 440                 445

Cys Gln Pro Leu Ala Val Val Asp Leu Ile Val Asp Ile Met Phe Ile
450                 455                 460

Val Asp Ile Leu Ile Asn Phe Arg Thr Thr Tyr Val Asn Ala Asn Glu
465                 470                 475                 480

Glu Val Val Ser His Pro Gly Arg Ile Ala Val His Tyr Phe Lys Gly
                485                 490                 495

Trp Phe Leu Ile Asp Met Val Ala Ala Ile Pro Phe Asp Leu Leu Ile
            500                 505                 510

Phe Gly Ser Gly Ser Glu Glu Leu Ile Gly Leu Leu Lys Thr Ala Arg
        515                 520                 525

Leu Leu Arg Leu Val Arg Val Ala Arg Lys Leu Asp Arg Tyr Ser Glu
530                 535                 540

Tyr Gly Ala Ala Val Leu Phe Leu Leu Met Cys Thr Phe Ala Leu Ile
545                 550                 555                 560

Ala His Trp Leu Ala Cys Ile Trp Tyr Ala Ile Gly Asn Met Glu Gln
                565                 570                 575

Pro His Met Asp Ser Arg Ile Gly Trp Leu His Asn Leu Gly Asp Gln
            580                 585                 590

Ile Gly Lys Pro Tyr Asn Ser Ser Gly Leu Gly Gly Pro Ser Ile Lys
        595                 600                 605

Asp Lys Tyr Val Thr Ala Leu Tyr Phe Thr Phe Ser Ser Leu Thr Ser
```

```
              610                 615                 620
Val Gly Phe Gly Asn Val Ser Pro Asn Thr Asn Ser Glu Lys Ile Phe
625                 630                 635                 640

Ser Ile Cys Val Met Leu Ile Gly Ser Leu Met Tyr Ala Ser Ile Phe
                645                 650                 655

Gly Asn Val Ser Ala Ile Ile Gln Arg Leu Tyr Ser Gly Thr Ala Arg
                660                 665                 670

Tyr His Thr Gln Met Leu Arg Val Arg Glu Phe Ile Arg Phe His Gln
            675                 680                 685

Ile Pro Asn Pro Leu Arg Gln Arg Leu Glu Glu Tyr Phe Gln His Ala
690                 695                 700

Trp Ser Tyr Thr Asn Gly Ile Asp Met Asn Ala Val Leu Lys Gly Phe
705                 710                 715                 720

Pro Glu Cys Leu Gln Ala Asp Ile Cys Leu His Leu Asn Arg Ser Leu
                725                 730                 735

Leu Gln His Cys Lys Pro Phe Arg Gly Ala Thr Lys Gly Cys Leu Arg
            740                 745                 750

Ala Leu Ala Met Lys Phe Lys Thr Thr His Ala Pro Pro Gly Asp Thr
        755                 760                 765

Leu Val His Ala Gly Asp Leu Leu Thr Ala Leu Tyr Phe Ile Ser Arg
    770                 775                 780

Gly Ser Ile Glu Ile Leu Arg Gly Asp Val Val Val Ala Ile Leu Gly
785                 790                 795                 800

Lys Asn Asp Ile Phe Gly Glu Pro Leu Asn Leu Tyr Ala Arg Pro Gly
                805                 810                 815

Lys Ser Asn Gly Asp Val Arg Ala Leu Thr Tyr Cys Asp Leu His Lys
                820                 825                 830

Ile His Arg Asp Asp Leu Leu Glu Val Leu Asp Met Tyr Pro Glu Phe
            835                 840                 845

Ser Asp His Phe Trp Ser Ser Leu Glu Ile Thr Phe Asn Leu Arg Asp
        850                 855                 860

Thr Asn Met Ile Pro Gly Ser Pro Gly Ser Thr Glu Leu Glu Gly Gly
865                 870                 875                 880

Phe Ser Arg Gln Arg Lys Arg Lys Leu Ser Phe Arg Arg Thr Asp
                885                 890                 895

Lys Asp Thr Glu Gln Pro Gly Glu Val Ser Ala Leu Gly Pro Gly Arg
            900                 905                 910

Ala Gly Ala Gly Pro Ser Ser Arg Gly Arg Pro Gly Gly Pro Trp Gly
        915                 920                 925

Glu Ser Pro Ser Ser Gly Pro Ser Ser Pro Glu Ser Ser Glu Asp Glu
    930                 935                 940

Gly Pro Gly Arg Ser Ser Ser Pro Leu Arg Leu Val Pro Phe Ser Ser
945                 950                 955                 960

Pro Arg Pro Pro Gly Glu Pro Pro Gly Gly Glu Pro Leu Met Glu Asp
                965                 970                 975

Cys Glu Lys Ser Ser Asp Thr Cys Asn Pro Leu Ser Gly Ala Phe Ser
                980                 985                 990

Gly Val Ser Asn Ile Phe Ser Phe Trp Gly Asp Ser Arg Gly Arg Gln
            995                 1000                1005

Tyr Gln Glu Leu Pro Arg Cys Pro Ala Pro Thr Pro Ser Leu Leu Asn
    1010                1015                1020

Ile Pro Leu Ser Ser Pro Gly Arg Arg Pro Arg Gly Asp Val Glu Ser
1025                1030                1035                1040
```

```
Arg Leu Asp Ala Leu Gln Arg Gln Leu Asn Arg Leu Glu Thr Arg Leu
            1045                1050                1055

Ser Ala Asp Met Ala Thr Val Leu Gln Leu Leu Gln Arg Gln Met Thr
        1060                1065                1070

Leu Val Pro Pro Ala Tyr Ser Ala Val Thr Thr Pro Gly Pro Gly Pro
    1075                1080                1085

Thr Ser Thr Ser Pro Leu Leu Pro Val Ser Pro Leu Pro Thr Leu Thr
    1090                1095                1100

Leu Asp Ser Leu Ser Gln Val Ser Gln Phe Met Ala Cys Glu Glu Leu
1105            1110            1115                1120

Pro Pro Gly Ala Pro Glu Leu Pro Gln Glu Gly Pro Thr Arg Arg Leu
            1125                1130                1135

Ser Leu Pro Gly Gln Leu Gly Ala Leu Thr Ser Gln Pro Leu His Arg
            1140                1145                1150

His Gly Ser Asp Pro Gly Ser
        1155
```